United States Patent [19]
Crossman et al.

[11] Patent Number: 6,106,537
[45] Date of Patent: Aug. 22, 2000

[54] SKIN PRICKERS

[75] Inventors: David Danvers Crossman, Christmas Common; Jeremy Marshall, Jericho, both of United Kingdom

[73] Assignee: Owen Mumford Limited, Oxford, United Kingdom

[21] Appl. No.: 09/202,897
[22] PCT Filed: Apr. 28, 1998
[86] PCT No.: PCT/GB98/01237
§ 371 Date: Dec. 22, 1998
§ 102(e) Date: Dec. 22, 1998
[87] PCT Pub. No.: WO98/48696
PCT Pub. Date: Nov. 5, 1998

[30] Foreign Application Priority Data

Apr. 28, 1997 [GB] United Kingdom ................... 9708512

[51] Int. Cl.⁷ .................................................. A61B 17/32
[52] U.S. Cl. ........................................... 606/181; 606/182
[58] Field of Search ................................. 606/181, 182, 606/148, 167

[56] References Cited

U.S. PATENT DOCUMENTS 4,469,110  9/1984  Slama ...................................... 128/770

FOREIGN PATENT DOCUMENTS 0 427 406   5/1991  European Pat. Off. .
WO 93/19671  10/1993  WIPO .

*Primary Examiner*—Michael Buiz
*Assistant Examiner*—Anthony S. King
*Attorney, Agent, or Firm*—Young & Thompson

[57] ABSTRACT

A skin pricker includes a barrel and a spring loaded lancet which can be primed and then fired, momentarily to project its tip. A finger projects laterally from the lancet through a slot in the barrel and this finger is pulled back past a catch to prime the device. A weak connection between the finger and lancet allows the finger to be bent until that connection breaks, thus firing the lancet. The finger may remain captive to the barrel.

17 Claims, 2 Drawing Sheets

SKIN PRICKERS

This application is a 371 of PCT/GB98/01237, filed Apr. 28, 1998. It also claims priority based on Great Britain patent application 9708512.0, filed Apr. 28, 1997.

BACKGROUND OF THE INVENTION

This invention relates to skin prickers for drawing small drops of blood for analysis. These have been developed so that they are cheap enough not only for the lancet whose tip penetrates skin to be thrown away after a single use, but the whole device which contains and fires the lancet can be discarded. Such wastage is justifiable in that it eliminates the risk of infection, sometimes fatal, from used lancets.

DESCRIPTION OF THE RELATED ART

These throw-away devices automatically retract the lancet after the tip has momentarily projected, and they are designed so that it is virtually impossible to get at the lancet after such use. However, such an objective is not always achieved, and by using a tool, for example, it is sometimes possible to reset the lancet.

Another problem facing the designer of such a device is to make it as simple as possible, with the minimum number of parts to manufacture and assemble. If the device is to be thrown away after a single use, anything too complex is unacceptable.

SUMMARY OF THE INVENTION

It is the aim of this invention to provide a skin pricker which is a "throwaway" after a single use, which is of very simple construction, and which, short of destruction, does make it virtually impossible to have access to the lancet after use.

According to the present invention there is provided a skin pricking device comprising a barrel containing a spring loaded lancet releasable from a primed rearward position momentarily to project its tip from the forward end of the barrel and then retract it, wherein the priming and release means for the lancet are combined in an element projecting laterally from the lancet through a longitudinal slot in the barrel, the element having a weakness enabling it to be broken off having been shifted rearwardly past a catch formation which retains it at a primed position at the rear end of the slot, the breaking off releasing the lancet.

Preferably, the projecting element is shaped between a break-off point adjacent the lancet and the portion that passes through the slot to maintain the element captive to the barrel after break-off. This shaping may take the form of a local enlargement forward of the break-off point that also serves as a fulcrum over which the projecting element at the primed position can be bent forwardly until breakoff.

Alternatively, or in addition, the rear end of the slot may provide a fulcrum over which the projecting element at the primed position can be bent rearwardly until it breaks. Thus the user may press the element forwards or pull it backwards.

The catch formation will conveniently be formed integrally with the barrel, which will normally be of moulded plastics.

It may include a rearwardly pointing resiliently flexible finger along a side of the slot creating towards its rear end a throat through which said element snaps by deflecting that rear end laterally of the slot. But preferably the catch formation comprises two rearwardly pointing fingers along opposite sides of the slot, convergent at their tips to form the throat. The or each finger may be formed so that, in its relaxed condition, its tip converges towards the other side of the slot.

The barrel conveniently comprises forward and rear parts which are brought together after the lancet has been located into the forward part. These parts can be integrally moulded from plastics material, being connected by a flexible bridge. When brought together the forward and rear parts are preferably bonded at the join permanently to trap the lancet and spring inside.

The slot may bridge both parts, in which case the or each finger may project rearwardly beyond the forward part and enter a forwardly opening recess in the wall of the rearward part which limits its flexure in the direction to widen the throat. The rear, closed end of the recess beyond the tip of the or each finger will provide a stop for the break-off element reaching the primed position. This arrangement enables the or each finger to be formed so that, in its relaxed condition, it is axially parallel with the barrel; and its convergence towards the other side of the slot is imposed by engagement with the mouth of said recess.

The lancet tip is preferably initially shrouded by a cap integrally moulded with the lancet body, the cap being insertable, on assembly of the device, in a non-retractable manner through the forward end of the barrel and there being breakable from the lancet body to allow the priming action. This makes the device safe from accidental firing.

BRIEF DESCRIPTION OF THE DRAWINGS

For a better understanding of the invention, one embodiment will now be described, by way of example, with reference to the accompanying drawing, in which.

DESCRIPTION OF THE PREFERRED EMBODIMENTS

Figure 1:
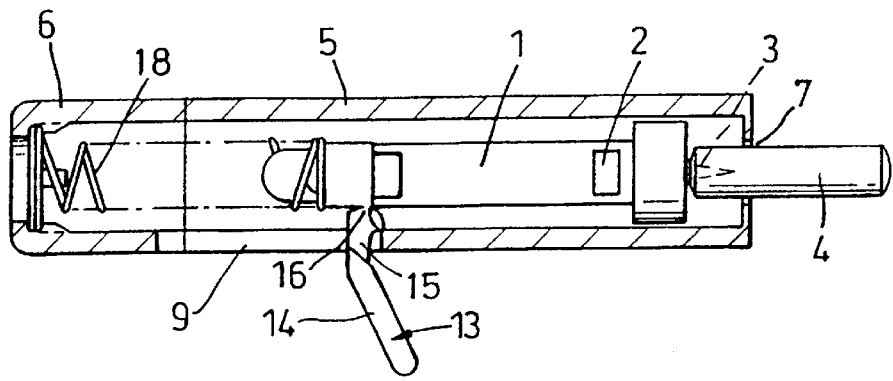
FIG. 1 is a longitudinal section of a skin pricker with its lancet in the pre-use condition.
Figure 2:
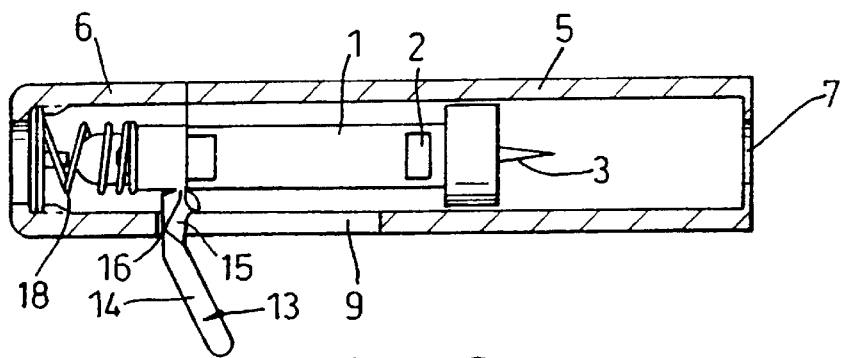
FIG. 2 is a longitudinal section of the pricker in the primed condition.
Figure 3:
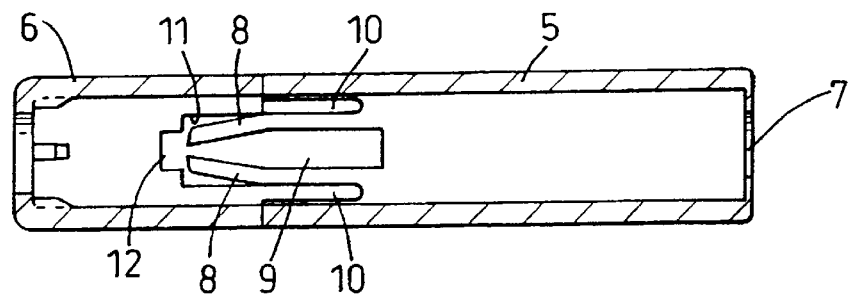
FIG. 3 is a longitudinal section of the body of the pricker, without the lancet, in a plane at right angles to that of FIGS. 1 and 2.

The lancet of FIG. 1 has a generally cylindrical body 1 of plastics material in which a needle 2 is co-axially embedded, its tip 3 projecting from the forward end. Initially, this is concealed in a break-off cap 4 of elongate form.

This lancet is carried in a barrel with an elongate forward part 5 and a shorter rear part 6 which initially are separated, although they can be integrally moulded as virtually separate items connected only by a thin flexible bridge. At the forward end the part 5 has an aperture 7 through which the cap 4 can be projected, but whose surround will provide on the inside a stop for the main lancet body 1 and on the outside a surface to abut the skin around the puncture point. At the rear end, the part 5 has two fingers 8 which project beyond it. They are largely formed by axially parallel slots 9 and 10 in the barrel wall, the flanking slots 10 being open to the rear end of the part 5 and the slot 9 between the fingers being similarly open but continuing to the tips of the fingers. In this embodiment, the fingers 8 are formed naturally to converge at their tips, thus narrowing the slot 9 towards its rear end. Both parts of the barrel are of moulded plastics material and the fingers 8 will have a certain resilient flexibility.

The rear part 6 has a recess 11 in its cylindrical wall opening forwardly. It is just deeper than the amount by which the fingers 8 project beyond the part 5 and it has a narrow extension 12 in its base. The circumferential width of the recess 11 corresponds to the distance between the outsides of these fingers 8. When the parts 5 and 6 are brought together, the fingers 8 enter this recess 11 and are circumferentially confined by it, while leaving the extension 12 just beyond the tips as a free space.

Figure 5:
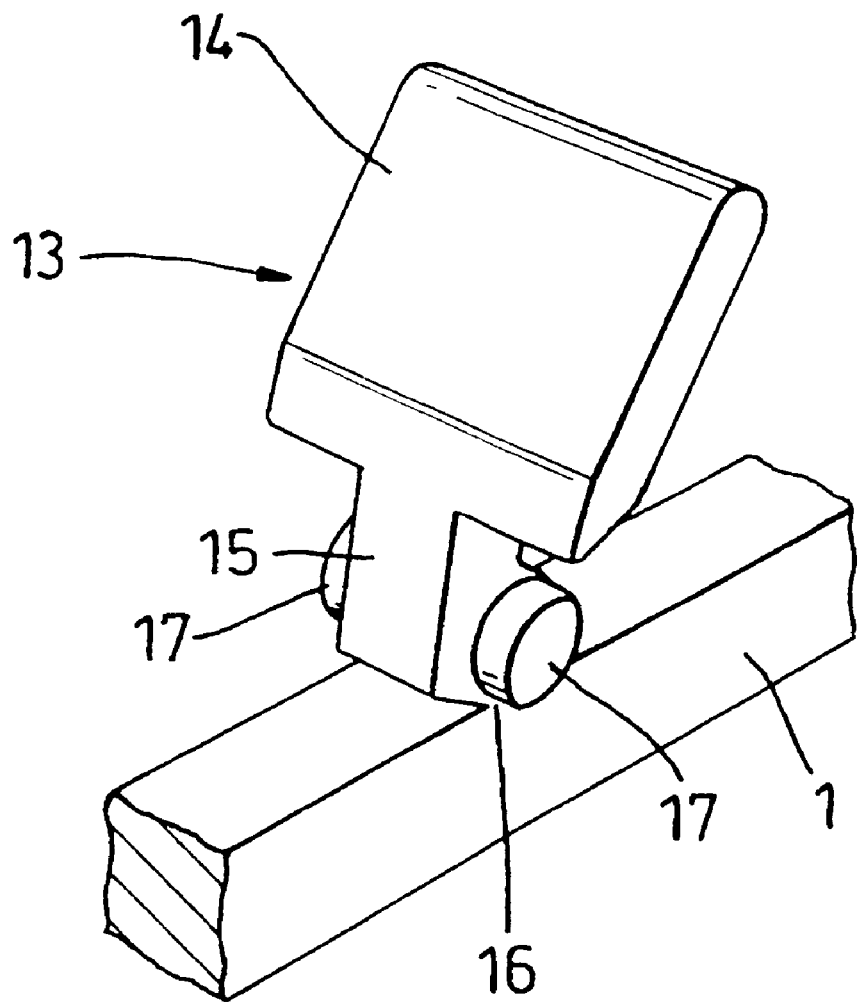
FIG. 5 is a perspective view of a priming and firing element.

Returning to the lancet and as best seen in FIG. 5, projecting laterally from the body 1 at the rear end there is a finger 13. Its outer portion 14 is a wide pad angled slightly forwardly and its inner portion 15, radial to the body 1, is of reduced width to fit easily within the slot 9. The base of the portion 15 is undercut to leave a narrow neck 16 by which the finger 13 is attached to the body 1, and immediately above this neck on the forward side there are laterally projecting lugs 17.

Figure 4:
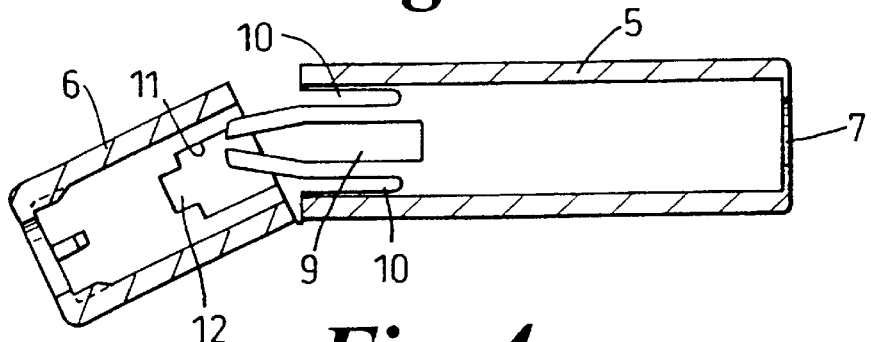
FIG. 4 is a section similar to FIG. 3 showing the manner of assembly.

Initially, the parts 5 and 6 are separated and the lancet is inserted in the forward part 5. The finger 13 is aligned with the slot 9 and the portion 15 between the lugs 17 and the pad 14 is passed through the tips of the fingers 8 as the cap 4 is projected through the aperture 7. A spring 18 is placed against the rear end of the lancet body 1, and the rear part 6 is closed over as shown in FIG. 4 with the other end of the spring being locked or bonded against the rear end of this part 6. The parts 5 and 6 are then bonded together.

To prime the device, the cap 4 is twisted off, the lancet body 1 being held against rotation by the finger 13. The tip 3 remains safe inside the barrel. Then the finger 13 is shifted rearwardly. This carries the lancet with it, compressing the spring 18. The resilience of the fingers 8 is such that the portion 15 can snap through the throat formed by the finger tips and enter the space 12 to be arrested by its blind end. But the fingers 8 re-converge and do not allow return, forward movement. The device is now primed.

To fire it, the pad 14 is pressed forwards and in towards the barrel. The finger 13 bends over the tips of the fingers 8, the lugs 17 acting as a fulcrum until the relatively weak narrow bridge 16 breaks. This releases the lancet; which shoots forward momentarily to project the needle tip 3. There is bounce back, leaving the tip safe inside the barrel, while the finger 13 is captive to the barrel by the lugs 17 being trapped under the sides of the recess extension 12. The device can then be discarded.

There is an alternative firing action, by pulling back on the finger 13 like a trigger. The blind end of the recess extension 12 then acts as a fulcrum over which the finger is bent until the bridge 16 breaks.

Instead of having the fingers 8 each formed with a bend or an inward curve, they could be axially parallel in their natural, relaxed state and their convergence could be imposed by the mouth of the recess 11 squeezing them together. This would make the initial insertion of the lancet into the part 5 slightly easier since the finger tips would not have to be held apart.

To prevent the device being primed with the cap 4 still in place, the cap may be formed with an arrowhead or barbed formation that allows it to be pressed through the aperture 7 from inside the barrel, but which prevents its return. It therefore has to be twisted off before the lancet can be retracted.

Instead of having two fingers 8 in a symmetrical arrangement, it would be possible to have just one resilient finger along one side of the slot, its tip being convergent towards the other side to form the throat through which the portion 14 is snapped in the priming action.

What is claimed is:

1. A skin pricking device comprising a barrel with an aperture at its leading end and a longitudinal slot in its side, a spring loaded lancet contained in the barrel, a priming and release element projecting laterally from the lancet through the slot, the element being connected to the lancet within the barrel by a neck of reduced cross-section in relation to the rest of the element, and a catch formation on the barrel past which the element can be shifted upon rearward movement along the slot, the catch formation then retaining the device primed, and the element being manipulable to break away from the lancet at the neck and thereby release the lancet for its tip momentarily to be projected through the aperture at the leading end of the barrel.

2. A device as claimed in claim 1, wherein the barrel comprises forward and rear parts which are brought together after the lancet has been loaded into the forward part.

3. A device as claimed in claim 2, wherein the slot bridges both parts.

4. A device as claimed in claim 3, wherein the or each finger projects rearwardly beyond the forward part and enters a forwardly opening recess in the wall of the rearward part which limits its flexure in the direction to widen the throat.

5. A device as claimed in claim 4, wherein the rear, closed end of the recess beyond the tip of the or each finger provides a stop for the break-off element reaching the primed position.

6. A device as claimed in claim 4, wherein the or each finger is formed so that, in its relaxed condition, it is axially parallel with the barrel, and its convergence towards the other side of the slot is imposed by engagement with the mouth of said recess.

7. A device as claimed in claim 2, wherein the forward and rear parts are integrally moulded from plastics material, and are connected by a flexible bridge.

8. A device as claimed in claim 7, wherein when brought together the forward and rear parts are bonded at the join permanently to trap the lancet and spring inside.

9. A device as claimed in claim 1, wherein the catch formation includes a rearwardly pointing resiliently flexible finger along a side of the slot creating towards its rear end a throat through which said element snaps by deflecting that rear end laterally of the slot.

10. A device as claimed in claim 9, wherein the catch formation comprises two rearwardly pointing fingers along opposite sides of the slot, convergent at their tips to form the throat.

11. A device as claimed in claim 9, wherein the or each finger is formed so that, in its relaxed condition, its tip converges towards the other side of the slot.

12. A device as claimed in claim 1, wherein the projecting element is shaped between the neck and the portion that passes through the slot to maintain the element captive to the barrel after break off.

13. A device as claimed in claim 12, wherein the shaping of the projecting element to maintain it captive is a local enlargement forward of the neck, the enlargement also serving as a fulcrum over which the projecting element at the primed position can be bent forwardly until break off.

14. A device as claimed in claim 1, wherein the rear end of the slot provides a fulcrum over which the projecting element at the primed position can be bent rearwardly until break-off.

15. A device as claimed in claim 1, wherein the catch formation is formed integrally with the barrel.

16. A device as claimed in claim 1, wherein the lancet tip is initially shrouded by a cap integrally moulded with the lancet body, the cap being insertable, on assembly of the device, in a non-retractable manner through the forward end of the barrel and there being breakable from the lancet body to allow the priming action.

17. A device as claimed in claim 1, wherein the barrel comprises forward and rear parts which are brought together after the lancet has been loaded into the forward part.

\* \* \* \* \*